US008084125B2

(12) United States Patent
Rizk

(10) Patent No.: US 8,084,125 B2
(45) Date of Patent: *Dec. 27, 2011

(54) NON-CURLING POLYHYDROXYALKANOATE SUTURES

(75) Inventor: Said Rizk, Salem, NH (US)

(73) Assignee: Tepha, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/636,129

(22) Filed: Dec. 11, 2009

(65) Prior Publication Data

US 2010/0093237 A1  Apr. 15, 2010

Related U.S. Application Data

(62) Division of application No. 11/193,580, filed on Jul. 29, 2005, now Pat. No. 7,641,825.

(60) Provisional application No. 60/598,296, filed on Aug. 3, 2004.

(51) Int. Cl.
*D02G 3/00* (2006.01)

(52) U.S. Cl. ............................. 428/364; 606/208

(58) Field of Classification Search .................. 428/364; 606/208
See application file for complete search history.

(56) References Cited

U.S. PATENT DOCUMENTS

| | | |
|---|---|---|
| 3,598,122 A | 8/1971 | Zaffaroni |
| 3,598,123 A | 8/1971 | Zaffaroni |
| 3,731,683 A | 5/1973 | Zaffaroni |
| 3,797,494 A | 3/1974 | Zaffaroni |
| 3,982,543 A | 9/1976 | Schmitt et al. |
| 4,031,894 A | 6/1977 | Urquhart et al. |
| 4,201,211 A | 5/1980 | Chandrasekaran et al. |
| 4,205,399 A | 6/1980 | Jamiolkowski et al. |
| 4,286,592 A | 9/1981 | Chandrasekaran |
| 4,314,557 A | 2/1982 | Chandrasekaran |
| 4,379,454 A | 4/1983 | Campbell et al. |
| 4,435,180 A | 3/1984 | Leeper |
| 4,537,738 A | 8/1985 | Holmes |
| 4,559,222 A | 12/1985 | Enscore et al. |
| 4,573,995 A | 3/1986 | Chen et al. |
| 4,588,580 A | 5/1986 | Gale et al. |
| 4,603,070 A | 7/1986 | Steel et al. |
| 4,645,502 A | 2/1987 | Gale et al. |
| 4,648,978 A | 3/1987 | Makinen et al. |
| 4,664,655 A | 5/1987 | Orentreich et al. |
| 4,704,282 A | 11/1987 | Campbell et al. |
| 4,711,241 A | 12/1987 | Lehmann |
| 4,758,234 A | 7/1988 | Orentreich et al. |
| 4,788,062 A | 11/1988 | Gale et al. |
| 4,792,336 A | 12/1988 | Hlavacek et al. |
| 4,816,258 A | 3/1989 | Nedberge et al. |
| 4,826,493 A | 5/1989 | Martini et al. |
| 4,849,226 A | 7/1989 | Gale |
| 4,853,226 A | 8/1989 | Machida et al. |
| 4,856,188 A | 8/1989 | Sibalis |
| 4,880,592 A | 11/1989 | Martini et al. |
| 4,908,027 A | 3/1990 | Enscore et al. |
| 4,910,145 A | 3/1990 | Holmes et al. |
| 4,938,763 A | 7/1990 | Dunn et al. |
| 4,943,435 A | 7/1990 | Baker et al. |
| 5,002,067 A | 3/1991 | Berthelsen et al. |
| 5,026,381 A | 6/1991 | Li |
| 5,032,638 A | 7/1991 | Wang et al. |
| 5,041,100 A | 8/1991 | Rowland et al. |
| 5,085,629 A | 2/1992 | Goldberg et al. |
| 5,124,371 A | 6/1992 | Tokiwa et al. |
| 5,128,144 A | 7/1992 | Korsatko-Wabnegg et al. |
| 5,171,308 A | 12/1992 | Gallagher et al. |
| 5,204,382 A | 4/1993 | Wallace et al. |
| 5,236,431 A | 8/1993 | Gogolewski et al. |
| 5,245,023 A | 9/1993 | Peoples et al. |
| 5,250,430 A | 10/1993 | Peoples et al. |
| 5,271,961 A | 12/1993 | Mathiowitz et al. |
| 5,278,201 A | 1/1994 | Dunn et al. |
| 5,278,202 A | 1/1994 | Dunn et al. |
| 5,278,256 A | 1/1994 | Bellis |
| 5,292,860 A | 3/1994 | Shiotani et al. |
| 5,306,286 A | 4/1994 | Stack et al. |
| 5,334,698 A | 8/1994 | Witholt et al. |
| 5,412,067 A | 5/1995 | Shinoda et al. |
| 5,443,458 A | 8/1995 | Eury |
| 5,468,253 A | 11/1995 | Bezwada et al. |
| 5,480,394 A | 1/1996 | Ishikawa |
| 5,480,794 A | 1/1996 | Peoples et al. |
| 5,489,470 A | 2/1996 | Noda |
| 5,502,116 A | 3/1996 | Noda |
| 5,502,158 A | 3/1996 | Sinclair et al. |
| 5,512,669 A | 4/1996 | Peoples et al. |
| 5,516,565 A | 5/1996 | Matsumoto |
| 5,516,883 A | 5/1996 | Hori et al. |
| 5,534,432 A | 7/1996 | Peoples et al. |

(Continued)

FOREIGN PATENT DOCUMENTS

CA  2307637  5/1999

(Continued)

OTHER PUBLICATIONS

Celanse, Textile Dictionary,p. 57 date 2001.*

(Continued)

*Primary Examiner* — N. Edwards
(74) *Attorney, Agent, or Firm* — Pabst Patent Group LL

(57) ABSTRACT

Absorbable polyester fibers, braids, and surgical meshes with improved handling properties have been developed. These devices are preferably derived from biocompatible copolymers or homopolymers of 4-hydroxybutyrate. These devices provide a wider range of in vivo strength retention properties than are currently available and have a decreased tendency to curl, in the preferred embodiment, due to the inclusion of relaxation and annealing steps following extrusion and orientation of the fiber. Filaments prepared according to these methods are characterized by the following physical properties: (i) elongation to break from about 17% to about 85% (ii) Young's modulus of less than 350,000 psi, (iii) knot to straight ratio (knot strength/tensile strength) of 55-80% or (iv) load at break from 1100 to 4200 grams.

7 Claims, No Drawings

U.S. PATENT DOCUMENTS

| | | | |
|---|---|---|---|
| 5,536,564 A | 7/1996 | Noda | |
| 5,550,173 A | 8/1996 | Hammond et al. | |
| 5,551,954 A | 9/1996 | Buscemi et al. | |
| 5,563,239 A | 10/1996 | Hubbs et al. | |
| 5,584,885 A | 12/1996 | Seckel | |
| 5,614,576 A | 3/1997 | Rutherford et al. | |
| 5,625,030 A | 4/1997 | Williams et al. | |
| 5,629,077 A | 5/1997 | Turnlund et al. | |
| 5,635,215 A | 6/1997 | Boschetti et al. | |
| 5,646,217 A | 7/1997 | Hammond | |
| 5,648,100 A | 7/1997 | Boschetti et al. | |
| 5,670,161 A | 9/1997 | Healy et al. | |
| 5,703,160 A | 12/1997 | Dehennau et al. | |
| 5,705,187 A | 1/1998 | Unger | |
| 5,709,854 A | 1/1998 | Griffith-Cima et al. | |
| 5,711,933 A | 1/1998 | Bichon et al. | |
| 5,728,752 A | 3/1998 | Scopelianos et al. | |
| 5,735,863 A | 4/1998 | Della Valle | |
| 5,753,364 A | 5/1998 | Rutherford et al. | |
| 5,753,708 A | 5/1998 | Koehler et al. | |
| 5,789,536 A | 8/1998 | Liggat et al. | |
| 5,811,272 A | 9/1998 | Snell et al. | |
| 5,814,071 A | 9/1998 | McDevitt et al. | |
| 5,814,599 A | 9/1998 | Mitragotri et al. | |
| 5,824,333 A | 10/1998 | Scopelianos et al. | |
| 5,824,751 A | 10/1998 | Hori et al. | |
| 5,834,582 A | 11/1998 | Sinclair et al. | |
| 5,840,331 A | 11/1998 | Van Cauter et al. | |
| 5,842,477 A | 12/1998 | Naughton et al. | |
| 5,855,619 A | 1/1999 | Caplan et al. | |
| 5,874,040 A | 2/1999 | Liggat et al. | |
| 5,876,452 A | 3/1999 | Athanasiou et al. | |
| 5,876,455 A | 3/1999 | Harwin | |
| 5,879,322 A | 3/1999 | Lattin et al. | |
| 5,919,478 A | 7/1999 | Landrau et al. | |
| 5,935,506 A | 8/1999 | Schmitz et al. | |
| 5,939,467 A * | 8/1999 | Wnuk et al. | 523/128 |
| 5,990,162 A | 11/1999 | Scharf | |
| 5,994,478 A | 11/1999 | Asrar et al. | |
| 6,056,970 A | 5/2000 | Greenawalt et al. | |
| 6,119,567 A | 9/2000 | Schindler et al. | |
| 6,214,387 B1 | 4/2001 | Berde et al. | |
| 6,245,537 B1 | 6/2001 | Williams et al. | |
| 6,316,262 B1 | 11/2001 | Huisman et al. | |
| 6,323,010 B1 | 11/2001 | Skraly et al. | |
| 6,454,811 B1 | 9/2002 | Sherwood et al. | |
| 6,514,515 B1 * | 2/2003 | Williams | 424/424 |
| 6,548,569 B1 | 4/2003 | Williams et al. | |
| 6,555,123 B2 | 4/2003 | Williams et al. | |
| 6,600,010 B2 | 7/2003 | Mao et al. | |
| 6,610,764 B1 | 8/2003 | Martin et al. | |
| 6,623,749 B2 | 9/2003 | Williams et al. | |
| 6,656,489 B1 | 12/2003 | Mahmood et al. | |
| 6,680,046 B1 | 1/2004 | Boschetti | |
| 6,770,356 B2 | 8/2004 | O'Donnell et al. | |
| 6,838,492 B2 | 1/2005 | Maleeny et al. | |
| 6,867,247 B2 | 3/2005 | Williams et al. | |
| 6,867,249 B2 * | 3/2005 | Lee | 524/4 |
| 6,878,248 B2 | 4/2005 | Signer et al. | |
| 6,878,758 B2 | 4/2005 | Martin et al. | |
| 7,108,716 B2 * | 9/2006 | Burnside et al. | 623/1.38 |
| 7,179,883 B2 | 2/2007 | Williams et al. | |
| 7,244,442 B2 | 7/2007 | Williams et al. | |
| 7,268,205 B2 | 9/2007 | Williams et al. | |
| 7,594,928 B2 * | 9/2009 | Headley et al. | 623/1.22 |
| 7,641,825 B2 * | 1/2010 | Rizk | 264/28 |
| 7,834,092 B2 * | 11/2010 | Uradnisheck et al. | 525/190 |
| 2002/0028243 A1 | 3/2002 | Masters | |
| 2002/0156150 A1 | 10/2002 | Williams et al. | |
| 2002/0173558 A1 | 11/2002 | Williams et al. | |
| 2003/0091803 A1 | 5/2003 | Bond et al. | |
| 2003/0185896 A1 | 10/2003 | Buiser et al. | |
| 2003/0211131 A1 | 11/2003 | Martin et al. | |
| 2005/0107505 A1 | 5/2005 | Shinoda et al. | |
| 2005/0267516 A1 | 12/2005 | Soleimani | |
| 2010/0009327 A1 * | 1/2010 | Brazil | 434/238 |
| 2010/0057123 A1 * | 3/2010 | D'Agostino et al. | 606/228 |

FOREIGN PATENT DOCUMENTS

| | | |
|---|---|---|
| CA | 2259098 | 7/1999 |
| CA | 2298421 | 2/2000 |
| DE | 39 37 649 | 5/1991 |
| EP | 0 258 781 | 3/1988 |
| EP | 0 344 704 | 12/1989 |
| EP | 0 349 505 | 3/1990 |
| EP | 0 423 484 | 4/1991 |
| EP | 0 429 403 | 5/1991 |
| EP | 0 432 443 | 6/1991 |
| EP | 0 452 111 | 10/1991 |
| EP | 0 507 554 | 10/1992 |
| EP | 0 601 885 | 6/1994 |
| EP | 0 628 586 | 12/1994 |
| EP | 0 754 467 | 1/1997 |
| EP | 1130043 | 9/2001 |
| EP | 1266984 | 12/2002 |
| GB | 2166354 | 5/1986 |
| JP | 62-209144 | 9/1987 |
| JP | 03-187386 | 8/1991 |
| JP | 04-292619 | 10/1992 |
| JP | 4-326932 | 11/1992 |
| JP | 5-023189 | 2/1993 |
| JP | 5-194141 | 11/1993 |
| JP | 06-264306 | 9/1994 |
| JP | 06-336523 | 12/1994 |
| JP | 7 275 344 | 10/1995 |
| JP | 08-089264 | 4/1996 |
| JP | 0 821 216 | 8/1996 |
| JP | 09-098793 | 4/1997 |
| JP | 09-507091 | 7/1997 |
| JP | 2000220032 | 8/2000 |
| WO | WO 92/18164 | 10/1992 |
| WO | WO 93/05824 | 4/1993 |
| WO | WO 93/20134 | 10/1993 |
| WO | WO 94/02184 | 2/1994 |
| WO | WO 94/06886 | 3/1994 |
| WO | WO 95/03356 | 2/1995 |
| WO | WO 95/17216 | 6/1995 |
| WO | WO 95/20614 | 8/1995 |
| WO | WO 95/20615 | 8/1995 |
| WO | WO 95/20621 | 8/1995 |
| WO | WO 95/23250 | 8/1995 |
| WO | WO 95/33874 | 12/1995 |
| WO | WO 96/00263 | 1/1996 |
| WO | WO 96/08535 | 3/1996 |
| WO | WO 96/18420 | 6/1996 |
| WO | WO 96/21427 | 7/1996 |
| WO | WO 96/40304 | 12/1996 |
| WO | WO 97/04036 | 2/1997 |
| WO | WO 97/07153 | 2/1997 |
| WO | WO 97/15681 | 5/1997 |
| WO | WO 97/30042 | 8/1997 |
| WO | WO 98/04292 | 2/1998 |
| WO | WO 98/39453 | 9/1998 |
| WO | WO 98/48028 | 10/1998 |
| WO | WO 98/51812 | 11/1998 |
| WO | WO 99/11196 | 3/1999 |
| WO | WO 99/14313 | 3/1999 |
| WO | WO 99/32536 | 7/1999 |
| WO | WO 99/35192 | 7/1999 |
| WO | WO 00/51662 | 9/2000 |
| WO | WO 00/56376 | 9/2000 |
| WO | WO 01/10421 | 2/2001 |
| WO | WO 01/15671 | 3/2001 |
| WO | WO 01/19361 | 3/2001 |
| WO | WO 02/085983 | 10/2002 |
| WO | WO 2004/101002 | 11/2004 |

OTHER PUBLICATIONS

Abate, et al., "Separation and structural characterizations of cyclic and open chain oligomers produced in the partial pyrolysis of microbial poly(hydroxyutyrates)", *Macromolecules*, 28(23):7911-1916 (1995).

Addolorato, et al., "Maintaining abstinence from alcohol with gamma-hydroxybutyric acid", *The Lancet*, 351:38 (1998).

Agostini, et al., "Synthesis and Characterization of Poly-βHydroxybutyrate. I. Synthesis of Crystalline DL Poly-β-Hydroxybutyrate from DL-β-Butyrolactone," *Polym. Sci., Part A-1,* 9:2775-87 (1971).

Akhtar, "Physiomechanical Properties of bacterial P(HB-HV) Polyesters and Their Uses in drug Delivery", The British Library Document Supply Centre, UMI, (1990).

Anderson, et al., "Occurrence, Metabolism, metabolic Role, and Industrial Uses of bacterial Polyhydroxyalkanoates", *Microbiological Reviews*, pp. 450-472 (1990).

Andriamampandry, et al., "Cloning of a rat brain succinic semialdehyde reductase involved in the synthesis of the neuromodulator g-hydroxybutyrate", *Biochem. J.*, 334:43-50 (1998).

Bailey, "Free radical ring-opening polymerization", *J. Polym. Preprints*, 25:210-11 (1984).

Bailey, et al., "Synthesis of Poly-ϵ-caprolactone via a free radical mechanism. Free radical ring-opening polymerization of 2-methylene-1,3-dioxepane", *J. Polym. Sci. Polym. Chem.*, 20:3021-30 (1982).

Bandiera, et al., "Effect of sodium sulfonate groups on the ionic conductivity of a copolyester of thiodipropionic acid", *Eur. Pol. J.*, 33:1679-1683 (1997).

Behrend, "PHB as a bioresorbable material for intravascular stents," *American J. Cardiol*. p. 45, TCT Abstracts (Oct. 1998).

Berde, et al., "Sustained release of dibucaine from a biodegradable polymer matrix: A potential method for prolonged neural blockade", Abstracts of Scientific Papers, 1990 Annual Meeting, Ameri. Soc. Anesthesiologists, 73(3A):A776, Sep. 1990.

Berger, et al, "PHB recovery by hypochlorite digestion of non-PHB biomass", *Biotechnonology Techniques*, 3(4):227-232 (1989).

Blight, "Miracles and molecules—progress in spinal cord repair.," *Nat. Neurosci* 5:1051-4 (2002).

Boeree, et al., "Development of a degradable composite for orthopaedic use: mechanical evaluation of an hydroxyapatite-polyhydroxybutyrate composite material", *Biomaterials*, 14(10):793-6 (1993).

Brandl, et al., "*Pseudomonas oleovorans* as a source of poly(b-hydroxyalkanoates for potential applications as biodegradable polyesters", *Appl. Environ. Microbiol.*, 54:1977-1982 (1988).

Braunegg, et al., "Polyhydroxyalkanoates, biopolyesters from renewable resources: physiological and engineering aspects", *J. Biotech.*, 65: 127-161 (1998).

Breuer, et al., "Tissue Engineering Lamb Heart Valve Leaflets," *Biotechnology & Bioengineering* 50:562-67 (1996).

Bruhn & Müller, "Preparation and characterization of spray-dried Poly(DL-Lactide) Micro Spheres", *Proceed. Intern. Symp. Control. Rel. Bioact. Mater.*, 18:668-69 (1991).

Byrom, "Miscellaneous Biomaterials," in *Biomaterials* (D. Byrom, ed.) pp. 333-359 MacMillan Publishers: London, 1991.

Campbell & Bailey, "Mechanical properties of suture materials in vitro and after in vivo implantation in horses," *Vet. Surg.* 21(5):355-61 (1992).

Chu, et al., *Wound Closure Biomaterials and Devices* CRC Press:Boca Raton, 1996.

Clavijo-Alvarez, et al. "Comparison of biodegradable conduits within aged rat sciatic nerve defects," *Plast Reconstr Surg.* 119(6):1839-51(2007).

Colombo, et al., "Involvement of GABA(A) and GABA(B) receptors in the mediation of discriminative stimulus effects of gamma-hydroxybutyric acid", *Physiology & Behavior*, 64:293-302 (1998).

Conti, et al., "Use of polylactic acid for the preparation of microparticulate drug delivery systems", *J. Microencapsulation*, 9:153-166 (1992).

Cookson, "It grows on trees", *Financial Times*, p. 6 (Aug. 12, 1992).

Cuebas, et al., "Mitochondrial metabolism of 3-mercaptopropionic acid. Chemical synthesis of 3-mercaptopropionyl coenzyme A and some of its S-acyl derivatives", *J. Biol. Chem.*, 260:7330-7336 (1985).

Damien & Parsons, "Bone graft and bone graft substitutes: a review of current technology and applications," *J. Appl. Biomater.* 2(3)187-208 (1991).

Dayton, et al., "Use of an absorbable mesh to repair contaminated abdominal-wall defects", *Arch Surg.*, 121:954-960 (1986).

De Groot, "Meniscal tissue regeneration in porous 50/50 copoly(L-lactide/epsilon-caprolactone) implants", *Biomaterials*, 18(8):613-22 (1997).

De Koning, et al., "A biodegradable rubber by crosslinking poly(hydroxyalkanoate) from *Pseudomonas oleovorans*", *Polymer*, 35:2090-97 (1994).

De Smet, et al., "Characterization of intracellular inclusions formed by *Pseudomonas oleovorans* during growth on octane", *J. Bacteriol.*, 154:870-78 (1983).

Domb, et al., *Handbook of Biodegradable Polymers* (Harwood Academic Publishers:Amsterdam, The Netherlands, 1997).

Dubois, et al., "Macromolecular Engineering of Polylactones and Polylactides. 12. Study of the Depolymerization Reactions of Poly(-caprolactone) with Functional Aluminum Alkoxide End Groups", *Macromolecules*, 26:4407-12 (1993).

Duvernoy, et al. "A biodegradable patch used as a pericardial substitute after cardiac surgery: 6- and 24-month evaluation with CT", *Thorac. Cardiovasc. Surg.*, 43(5):271-74 (1995).

Encyclopedic Handbook of Biomaterials and Bioengineering, Part A: Materials, vol. 1 eds. Wise, et al.; Marcel Dekker, Inc., New York, 1995.

Entholzner, et al., "EEG changes during sedation with gamma-hydroxybutyric acid", *Anaesthesist*, 44:345-350 (1995).

Fraser, et al., "Controlled release of a GnRH agonist from a polyhydroxybutyric acid implant-reversible suppression of the menstrual cycle in the macaque," *Acta Endocrinol* 121:841-848 (1989).

Freed, et al., "Biodegradable polymer scaffolds for tissue engineering", *Biotechnology*, 12:689-693 (1994).

Füchtenbusch, et al., "Biosynthesis of novel copolyesters containing 3-hydroxypivalic acid by *Rhodoccus ruber* NCIMB 40126 and related bacteria", *FEMS Microbiol. Lett.*, 159:85-92 (1998).

Fukuzaki, et al., "Direct copolymerization of L-lactic acid with ÿ-butyrolactone in the absence of catalysts", *Die Madromoleculare Chemie*, 190:1553-59 (1989).

Gabbay, et al, "New outlook on pericardial substitution after open heart operations", *Ann. Thorac. Surg.*, 48(6):803-12 (1989).

Gagnon, et al., "A thermoplastic elastomer produced by the bacterium *Pseudomonas oleovarans*", *Rubber World*, 207:32-38 (1992).

Gagnon, et al., "Chemical modification of bacterial elastomers: 1. Peroxide crosslinking", *Polymer*, 35:4358-67 (1994).

Gagnon, et al., "Chemical modification of bacterial elastomers: 2. Sulfur vulvanization", *Polymer*, 35:4368-75 (1994).

Gerngross & Martin, "Enzyme-catalyzed synthesis of poly[(R)-(-)-3-hydroxybutyrate]: formation of macroscopic granules in vitro," *Proc. Natl. Acad. Sci.* USA, 92:6279-83 (1995).

Gerra, et al., "Flumazenil effects on growth hormone response to gamma-hydroxybutyric acid", *International Clinical Psychopharmacology*, 9:211-215 (1994).

Griebel, et al., "Metabolism of poly-beta-hydroxybutyrate. I. Purification, composition, and properties of native poly-beta-hydroxybutyrate granules from *Bacillus megaterium*", *Biochemistry*, 7:3676-3681 (1968).

Gross, et al., "Polymerization of β-Monosubstituted-β-propiolactones Using Trialkylaluminum-Water Catalytic Systems and Polymer Characterization", *Macromolecules*, 21:2657-68 (1988).

Gugala, et al., Regeneration of segmental diaphyseal defects in sheep tibiae using resorbable polymeric membranes: a preliminary study, *J. Orthop. Trauma*. 13(3):187-95 (1999).

Gürsel, et al., "In vivo application of biodegradable controlled antibiotic release systems for the treatment of implant-related osteomyelitis," *Biomaterials* 22: 73-80 (2001).

Hadlock, et al., "Ocular cell monolayers cultured on biodegradable substrates," *Tissue Eng.* 5(3):187-96 (1999).

Hazari, et al., "A new resorbable wrap-around implant as an alternative nerve repair technique", *J. Hand Surgery*, 24(3): 291-295 (1999).

Hazari, et al., "A resorbable nerve conduit as an alternative to nerve autograft in nerve gap repair", *Br J Plast Surg.*, 52(8):653-7 (1999).

Hein, at al, "Biosynthesis of poly(4-hydroxybutyric acid) by recombinant strains of *Escherichia coli*," *FEMS Microbiol. Lett.* 153:411-18 (1997).

Heydorn, et al., "A new look at pericardial substitutes," *J. Thorac. Cardiovasc. Surg.* 94:291-96 (1987).

Hocking & Marchessault, "Biopolyesters" in *Chemistry and Technology of Biodegradable Polymers*, (G.J.L. Griffin, ed.), pp. 48-96, Chapman and Hall: London, 1994.

Hocking & Marchessault, "Syndiotactic poly[(R,S)-β-hydroxybutyrate] isolated from methyaluminoxane-catalyzed polymerization", *Polym. Bull.*, 30:163-70 (1993).

Hoke, "Mechanisms of Disease: what factors limit the success of peripheral nerve regeneration in humans?" *Nat. Clin. Pract. Neurol.* 448-454 (2006).

Holmes, "Biologically Produced (R)-3-hydroxyalkanoate Polymers and Copolymers", in *Developments in Crystalline Polymers* (Bassett, ed.), pp. 1-65, Elsevier: London, 1988.

Holmes, et al., "Applications of PHB—a microbially produced biodegradable thermoplastic," *Phys Technol* 16:32-36 (1985).

Hori, et al., "Chemical synthesis of high molecular weight poly(3-hydroxybutyrate-co-4-hydroxybutyrate)", *Polymer*, 36:4703-05 (1995).

Hori, et al., "Ring-Opening Copolymerization of Optically Active β-Butyrolactone with Several Lactones Catalyzed by Distannoxane Complexes: Synthesis of New Biodegradable Polyesters", *Macromolecules*, 26:4388-90 (1993).

Hori, et al., "Ring-Opening Polymerization of Optically Active β-Butyrolactone Using Distannoxane Catalysts: Synthesis of High Molecular Wright Poly(3-hydroxybutyrate)", *Macromolecules*, 26:5533-34 (1993).

Horowitz, et al., "Novel Thermal Route to an Amorphous, Film-Forming Polymer Latex", *Macromolecules*, 32:3347-3352 (1999).

Horsch, "Inheritance of functional foreign genes in plants", *Science*, 223:496-498 (1984).

Huijberts, et al., "Pseudomonas putida KT2442 cultivated on glucose accumulates poly(3-hydroxyalkanoates) consisting of saturated and unsaturated monomers", *Appl Environ Microbiol.*, 58(2):536-44 (1992).

Hutmacher, et al., "A review of material properties of biodegradable and bioresorbable polymers and devices for GTR and GBR applications," *Int. J. Oral Maxillofac. Implants*, 11(5):667-78 (1996).

Kameyama, et al., "Novel sequence-ordered polymers by transformation of polymer backbone: Quantitative and regioselective insertion of Thiranes into poly( S-aryl thioester)", *Macromol.*, 32:1407-1412 (1999).

Kassab, "Rifampicin carrying polyhydroxybutyrate microspheres as a potential chemoembolization agent", Journal of Biomaterials Science, Polymer Edition, 8(12):947-961 (1997).

Kassab, et al., "Embolization with polyhydroxybutyrate (PHB) microspheres: in vivo studies", *J. Bioact. Compat. Polym.*, 14:291-303 (1999).

Kaufman and Nelson, "An overview of gamma-hydroxybutyrate catabolism: the role of the cytosolic NADP(+)-dependent oxidoreductase EC 1.1.1.19 and of a mitochondrial hydroxyacid-oxoacid transhydrogenase in the initial, rate-limiting step in this pathway", *Neurochemical Research*, 16:965-974 (1991).

Keeler, "Don't Let Food Go To Waste—Make Plastic Out of It", *R&D Magazine*, pp. 52-57 (1991).

Keeler, "Plastics Grown in Bacteria Inch Toward the Market", *R&D Magazine*, pp. 46-52 (1991).

Kemnitzer, et al., "Preparation of predominantly Syndiotactic Poly(β-hydroxybutyrate) by the Tributylin Methoxide Catalyzed Ring-Opening Polymerization of racemic β-Butyrolactone", *Macromolecules*, 26:1221-29 (1993).

Kim and Mooney, "Engineering smooth muscle tissue with a predefined structure", *J. Biomed. Mat. Res.*, 41(2):322-332 (1998).

Kishida, et al. "Formulation assisted biodegradeable polymer matrices" *Chemical and Pharmaceutical Bulletin, JP Pharm Society of Japan.* 37(7):1954-1956(1989).

Kleinschmidt, et al., "Continuous sedation during spinal anaesthesia: gamma-hydroxybutyrate vs. propofol", *European Journal of Anaesthesiology*, 16:23-30 (1999).

Kleinschmidt, et al., "Total intravenous anaesthesia using propofol, gamma-hydroxybutyrate or midazolam in combination with sufentanil for patients undergoing coronary artery bypass surgery", *European Journal of Anesthesiology*, 14:590-599 (1997).

Klinge, et al., "Functional assessment and tissue response of short- and long-term absorbable surgical meshes", *Biomaterials*, 22:1415-1424 (2001).

Koosha, "Preparation and characterization of biodegradable polymeric drug carriers", Ph.D. Dissertation, 1989, Univ. Nottingham, UK., *Diss. Abstr. Int., B* 51:1206 (1990).

Koosha, et al., "Polyhydroxybutyrate as a drug carrier", *Crit. Rev. Ther. Drug Carrier Syst.*, 6(2):117-30 (1989).

Korkusuz, et al., In vivo response to biodegradable controlled antibiotic release systems, *J. Biomed. Mater. Res.* 55: 217-228 (2001).

Korsatko, et al., "The influence of the molecular weight of poly-D(−)-3-hydroxybutyric acid on its use as a retard matrix for sustained drug release," *8th Europ. Congress of Biopharmaceutics and Pharmokinetics* 1:234-242 (1987).

Korte & Gelt, "Hochdruckreaktionen. II. Die Polymerisation Von γ butyrolacton und γ-valerolactam bei hohen drücken", *Polymer Lett.*, 4:685-89 (1966).

Kusaka, et al., "Microbial synthesis and Physical Properties of ultra-high-molecular-weight poly[(R)-3-hydroxybutyrate]", *Pure Appl. Chem.*, A35:319-35 (1998).

Lafferty, et al., "Microbial Production of Poly-b-hydroxybutyric acid", in *Biotechnology* (Rehm & Reed, Eds.), pp. 135-176, Verlagsgesellschaft:Weinheim, 1988.

Lamba, et al., "Degradation of polyurethanes", in *Polyurethanes in Biomedical Applications* (CRC Press:Boca Raton, Florida, 1998).

Lanza, et al., *Principles of Tissue Engineering* (Academic Press:Austin, 1997).

Le Borgne, et al., "Stereoelective polymerization of β-butyrolactone", *Polymer*, 30:2312-19 (1989).

Lebedev and Yevstropov, "Thermoplastic properties of polylactones", *Makromol. Chem.*, 185:1235-1253 (1984).

Lee, et al., "Copolymerization of ÿ-butyrolactone and β-butyrolactone", *Macromol. Chem. Phys.*, 198:1109-20 (1997).

Lemoigne & Roukhelman, "Fermetation β-Hydroxybutyrique Caracterisation et Evolution Des Produits de Deshydration et de Polymerisation de L'acide β-Dehydroxybutyrique", *Annales des fermentations*, 5:527-36 (1925).

Ljungberg, et al. "Neuronal survival using a resorbable synthetic conduit as an alternative to primary nerve repair", *Microsurgery*, 19(6):259-264 (1999).

Lloyd, et al., "Transformation of *Arabidopsis thalania* with *Agrobacterium tumefaciens*", *Science*, 234: 464-66 (1986).

Lütke-Eversloh et al., "Identification of a new class of biopolymer: Bacterial synthesis of a sulfur-containing polymer with thioester linkages", *Microbiology*, 147(1): 11-19 (2001).

Lütke-Eversloh et al., "List of submitted abstracts", *The 8th International Symposium on Biological Polyesters*, (2000).

Madison & Huisman, "Metabolic engineering of poly(3-hydroxyalkanoates): from DNA to plastic", *Microbiol. Molec. Biol. Rev.*, 63:21-53 (1999).

Malm, et al., "A new biodegradable patch for closure of atrial septal defect. An experimental study", *Scand. J. Thorac. Cardiovasc. Surg.*, 26(1):9-14 (1992).

Malm, et al., "Enlargement of the right ventricular outflow tract and the pulmonary artery with a new biodegradable patch in transannular position", *Eur. Surg. Res.*, 26(5):298-308 (1994).

Malm, et al., "Prevention of postoperative pericardial adhesions by closure of the pericardium with absorbable polymer patches. An experimental study", *J. Thorac. Cardiovasc. Surg.*, 104(3):600-07 (1992).

Martin and Williams, "Medical application of poly-4-hydroxybutyrate: A strong flexible absorbable biomaterial", *Biochem. Eng. J.*, 16:97-105 (2003).

Mathiowitz & Langer, "Polyanhydride microspheres as drug delivery systems", in *Microcapsules Nanopart. Med. Pharm.* (Donbrow, ed.), pp. 99-123 (CRC:Boca Raton, Florida, 1992).

Maysinger, et al., "Microencapsulation and the Grafting of Genetically Transformed Cells as Therapeutic Strategies to rescue Degenerating Neurons of the CNS", *Reviews in the Neurosciences*, 6:15-33 (1995).

McMillin, et al., "Elastomers for Biomedical Applications," *Rubber Chemistry and Technology*, 67:417-446 (1994).

McWiliams, "Plastics as high as an elephant's eye?" *Business Week*, pp. 110-111 (Aug. 19, 1991).

Modelli, et al., "Kinetics of aerobic polymer degradation in soil by means of the ASTM D 5988-96 standard method," *J Environ Polym Degr* 7:109-116 (1999).

Müh, et al., "PHA synthase from chromatium vinosum: cysteine 149 is involved in covalent catalysis", *Bioche.*, 38:826-837 (1999).

Müller, et al., "Poly(hydroxyalkanoates): A Fifth Class of Physiologically Important Organic Biopolymers", *Angew. Chem. Int. Ed. Engl.*, 32:477-502 (1993).

Nakamura et al., "Biosynthesis and characteristics of bacterial poly(3-hydroxybutyrate-co-3-hydroxypropionate)", *Macromol. Rep.*, A28, 15-24 (1991).

Nakamura, et al., "Microbial synthesis and characterization of poly(3-hydroxybutyrate-co-4-hydroxybutyrate)", *Macromol.*, 25:4237-41 (1992).

Nelson, et al., "The extraneural distribution of gamma-hydroxybutyrate", *J. Neurochem.*, 37:1345-1348 (1981).

Niklason, et al., "Functional arteries grown in vitro," *Science* 284(5413):489-93 (1999).

Nobes, et al., "Polyhydroxyalkanoates: Materials for delivery systems", *Drug Del.*, 5:167-77 (1998).

Ogawa, et al., "A New Technique to Efficiently Entrap Leuprolide Acetate into Microcapsules of Poly Lactic Acid or Copoly(Lactic/Glycolic) Acid", *Chem. Pharm. Bull.*, 36:1095-103 (1988).

Otera, et al., "Distannoxane as reverse micelle-type catalyst: novel solvent effect on reaction rate of transesterification", *J. Org. Chem.*, 54:4013-14 (1989).

Otera, et al., "Distannoxane-catalysed transesterification of 1, n-Dioldiacetates. Selective transformation of either of chemically equivalent functional groups", *J. Chem. Soc. Chem. Commun.*, 1742-43 (1991).

Otera, et al., "Novel distannoxane-catalyzed transesterification and a new entry to ÿ,ÿ-unsaturated carboxylic acids", *Tetrahedron Lett.*, 27:2383-86 (1986).

Otera, et al, "Novel template effects of distannoxanne catalysts in highly efficient transesterification and esterification", *J. Org. Chem.*, 56:5307-11 (1991).

Pedrós-Alio et al., "The influence of poly-b-hydroxybutyrate accumulation on cell volume and buoyant density in *Alcaligenes eutrophus*", *Arch. Microbiol.* 143:178-184 (1985).

Peoples, et al., "Poly-β-hydroxybutyrate Biosynthesis in *Alcaligenes eutrophus* H16", *J. Biol. Chem*, 264(26):15293-97 (1989).

Peoples, et al., "Polyhydroxybutyrate (PHB): A Model System for Biopolymer Engineering: II", in *Novel Biodegradable Microbial Polymers* (Dawes, ed.) pp. 191-202, Kluwer Academic Publishers:Netherlands (1990).

Perrin & English, "Polycaprolactone", in *Handbook of Biodegradable Polymers* (Domb, et al., eds.) pp. 63-77 (Harwood, Amsterdam, 1997).

Pinto, "Hydrogen Peroxide as depyrogenation agent for medical devices components", *Revista De Saude Publica*, 29(1):75-79 (1995).

Poirier, "Perspectives on the production of polyhydroxyalkanoates in plants", *FEMS Microbiology Reviews*, 103:237-46 (1992).

Poirier, et al., "Progress Toward Biologically Produced Biodegradable thermoplastics", *Adv. Mater.*, 5(1):30-37 (1993).

Pool, "In Search of the Plastic Potato", *Science*, 245: 1187-89 (1989).

Pouton & Akhtar, "Biosynthetic polyhydroxyalkanoates and their potential in drug delivery", *Adv. Drug Delivery Rev.*, 18:133-62 (1996).

Rehm and Steinbüchel, "Biochemical and genetic analysis of PHA synthases and other proteins required for PHA synthesis", *Int. J. Biol. Macromol.* 25:3-19 (1999).

Renstad, et al., "The influence of processing induced differences in molecular structure on the biological and non-biological degradation of poly (3-hydroxybutyrate-co-3-hydroxyvalerate), P(3-HB-co-3-HV)," *Polymer Degradation and Stability* 63:201-211 (1999).

Reynolds, *Martindale: The Extra Pharmacopeia*, p. 1264, (Thirty First Edition, Royal Pharmaceutical Society, London, 1997).

Rivard, et al., "Fibroblast seeding and culture in biodegradable porous substrates", *J. Appl. Biomater.*, 6(1):65-68 (1995).

Ropero-Miller & Goldberger, "Recreational drugs. Current trends in the 90s", *Clinics in Laboratory Medicine*, 18:727-746 (1998).

Sabbagh, et al., "3-Mercaptopropionic acid, a potent inhibitor of fatty acid oxidation in rat heart mitochondria", *J. Biol. Chem.* 260:7337-7342 (1985).

Saito, et al., "Microbial synthesis and properties of poly(3-hydroxybutyrate-co-4-hydroxybutyrate) in *Comamonas acidovorans*", *Int. J. Biol. Macromol.*, 16(2):99-104 (1994).

Scharf, et al., "Pharmacokinetics of gammahydroxybutyrate (GHB) in narcoleptic patients", *Sleep* 21:507-514 (1998).

Schlegel, et al., "Ein submersverfahren zur kultur wasserstoffoxydierender bakterien: Wachstumsphysiologische untersuchungen", *Arch. Mikrobiol.* 38:209-222 (1961).

Schlosshauer, "Synthetic nerve guide implants in humans: a comprehensive survey." *Neurosurgery* 59:740-748 (2006).

Schmidt, et al "Neural tissue engineering: strategies for repair and regeneration," *Annu. Rev. Biomed. Eng.* 5:293-347 (2003).

Schwartz & Goodman, *Plastic Materials and Processes*, (Van Nostrand Reinhold Company:New York, 1982).

Sendelbeck & Girdis, "Disposition of a 14C-labeled bioerodible polyorthoester and its hydrolysis products, 4-hydroxybutyrate and cis,trans-1,4-bis(hydroxymethyl)cyclohexane, in rats", *Drug Metabolism & Disposition* 13:291-295 (1985).

Shin'Oka & Mayer, "New frontiers in tissue engineering: tissue engineered heart valves", in *Synthetic Biodegradable Polymer Scaffolds* (Atala & Mooney, eds.) pp. 187-198 Birkhäuser Boston, 1997.

Shinoka, et al., "Creation of viable pulmonary artery autografts through tissue engineering," *J. Thorac. Cardiovasc. Surg.* 115(3):536-46 (1998).

Shinoka, et al., "Tissue engineering heart valves: valve leaflet replacement study in a lamb model" *Ann. Thorac. Surg.* 60(6 Suppl):S513-16 (1995).

Sim, et al., "PHA synthase activity controls the molecular weight and polydispersity of polyhydroxybutyrate in vivo", *Nat. Biotechnol.*, 15(1):63-67 (1997).

Skrede et al, "Thia fatty acids, metabolism and metabolic effects" in *Biochim Biophys Acta*, 1344:115-31 (1997).

Snead, "The gamma-hydroxybutyrate model of absence seizures: correlation of regional brain levels of gamma-hydroxybutyric acid and gamma-butyrolactone with spike wave discharges", *Neuropharmacology* 30:161-167 (1991).

Song, et al., "Production of poly(4-hydroxybutyric acid) by fed-batch cultures of recombinant strains of *Escherichia coil*", *Biotechnol. Lett.* 21:193-197 (1999).

Speer & Warren, "Arthroscopic shoulder stabilization. A role for biodegradable materials," *Clin. Orthop.* (291):67-74 (1993).

Stanton & Gagné, "The remarkable catalytic activity of alkali-metal alkoxide clusters in the ester interchange reaction", *J. Am. Chem. Soc.*, 119:5075-76 (1997).

Steinbüchel & Valentin, "Diversity of bacterial polyhydroxyalkanoic acids," *FEMS Microbiol. Lett.*, 128:219-28 (1995).

Steinbüchel & Wiese, "A *Pseudomonas* strain accumulating polyesters of 3-hydroxybutyric acid and medium-chain-length 3-hydroxyalkanoic acids", *Appl. Microbial. Biotechnol.*, 37:691-97 (1992).

Steinbüchel, "Molecular basis for biosynthesis and accumulation of polyhydroxyalkanoic acids in bacteria", *FEMS Microbial. Rev.*, 103:217-230 (1992).

Steinbüchel, "Polyhydroxyalkanoic Acids", in *Biomaterials* (D. Byrom ed.), pp. 123-213, MacMillan Publishers:.London, 1991.

Takagi et al., "Biosynthesis of polyhydroxyalkanoate with a thiophenoxy side group obtained from Pseudomonas putida", *Macromolecules*, 32: 8315-8318 (1999).

Talja, et al., "Bioabsorbable and biodegradable stents in urology," *J. Endourol.* 11(6):391-97 (1997).

Tanahashi, et al., "Thermal Properties and Stereoregularity of Poly(3-hydroxybutyrate) Prepared from optically Active β-Butyrolactone with a Zinc-Based Catalyst", *Macromolecules*, 24:5732-33 (1991).

Tanaka, et al., "Clinical application of 4-hydroxybutyrate sodium and 4-butyrolactone in neuropsychiatric patients", *Folia Psychiatrica et Neurologica* 20:9-17 (1966).

Tanguay, et al., "Current status of biodegradable stents," *Cardiol. Clin.* 12(4):699-713 (1994).

Tepha announces submission of device master file to FDA (Jun. 3, 2002), Retrieved Dec. 17, 2004, from http://www.pressrelease.be/script_UK/newsdetail.asp?ndays=m&ID=695.

Tepha submits device master file to FDA—New Technology (Jul. 2, 2002). Retrieved on Dec. 17, 2004, from http://www.findarticles.com/p/articles/mi_mOPC/is_7_26/ai_89018276.

Tsuruta, et al., *Biomedical Applications of Polymeric Materials* (CRC Press, Boca Raton, Florida, 1993).

Tunnicliff, "Sites of action of gamma-hydroxybutyrate (GHB)—a neuroactive drug with abuse potential", *Clinical Toxicology*, 35:581-590 (1997).

Türesin, et al., "Biodegradable polyhydroxyalkanoate implants for osteomyelitis therapy: in vitro antibiotic release," *J. Biomater. Sci. Polymer Edn.* 12: 195-207 (2001).

Turke, "Absorbable Biomaterial is suited for diverse applications" (Jun. 3, 2002). Retrieved on Dec. 17, 2004, from http:www.devicelink.com/mpmn/archive/01/10/009.html.

Unverdorben, et al., "Polyhydroxybutyrate (PHB) Biodegradable Stent-Experience in the Rabbit," *American J. Cardiol.* p. 46, TCT Abstracts (Oct. 1998).

Valappil, et al., "Biomedical applications of polyhydroxyalkanoates, an overview of animal testing and in vivo responses", *Expert Rev. Med. Devices*, 3(6):853-868 (2006).

Valentin, et al., "Production of poly(3-hydroxybutyrate-co-4-hydroxybutyrate) in recombinant *Escherichia coil* grown on glucose," *J. Biotechnol.* 58:33-38 (1997).

Valentin, et al., "Identification of 4-hydroxyhexanoic acid as a new constituent of biosynthetic polyhydroxyalkanoic acids from bacteria", *Appl. Microbiol. Biotechnol.*, 40:710-16 (1994).

Valentin, et al., "Identification of 4-hydroxyvaleric acid as a constituent of biosynthetic polyhydroxyalkanoic acids from bacteria", *Appl. Microbiol. Biotechnol.*, 36:507-514 (1994).

Valentin, et al., "Identification of 5-hydroxyhexanoic acid, 4-hydroxyaheptanoic acid and 4-hydroxyoctanoic acids as new constituents of bacterial polyhydroxyalkanoic acids", *Appl. Microbiol. Biotechnol.*, 46:261-67 (1996).

Von Schroeder, et al., "The use of polylactic acid matrix and periosteal grafts for the reconstruction of rabbit knee articular defects," *J. Biomed. Mater. Res.* 25(3):329-39 (1991).

Walled & Rohwedder, "Poly-β-hydroxyalakaonate from Activated Sludge", *Environ. Sci. Technol.*, 8:576-79 (1974).

Widmer & Mikos, "Fabrication of biodegradable polymer scaffolds for tissue engineering" in *Frontiers in Tissue Engineering* (Patrick, et al., Eds.) Ch. II.5, pp. 107-120 (Elsevier Science, New York, 1998).

Williams & Peoples, "Biodegradable plastics from plants", *Chemtech*, 26:38-44 (1996).

Williams & Peoples, "Making plastics green", *Chem. Br.*, 33:29-32 (1997).

Williams, et al, "Application of PHAs in Medicine and Pharmacy", *Polyesters, III*, 4:91-127 (2002).

Williams, et al., "PHA applications: addressing the price performance issue. I. Tissue engineering," *Int. J. Biol. Macromol.* 25(1-3): 111-121 (1999).

Williams, et al., "PHA applications: addressing the price performance issue. I. Tissue engineering", *Int. J. Biol. Macromol.*, 25(1-3): 111-121 (1999).

Wodzinska, et al., "Polyhydroxybutyrate synthase: Evidence for covalent catalysis", *J. Am. Chem. Soc.* 118:6319-6320 (1996).

Wong & Mooney, "Synthesis and properties of biodegradable polymers used as synthetic matrices for tissue engineering", in *Synthetic Biodegradable Polymer Scaffolds* (Atala, et al., eds.) pp. 51-82 (Birkhäuser: Boston, 1997).

Worsey and Williams, "Metabolism of toluene and xylenes by *Pseudomonas putida* (*arvilla*) mt-2: evidence for a new function of the TOL plasmid" *J Bacteriol* 124:7-13 (1975).

Xie, et al., "Ring-opening Polymerization of β-Butyrolactorte by Thermophilic Lipases", *Macromolecules*, 30:6997-98 (1997).

Yagmurlu, et al., "Sulbactam-cefoperazone polyhydroxybutyrate-co-hydroxyvalerate (PHBV) local antibiotic delivery system: in vivo effectiveness and biocompatibility in the treatment of implant-related experimental osteomyelitis", *J Biomed Mater Res.*, 46(4):494-503 (1999).

Yamada, et al., "Development of a dural substitute from synthetic bioabsorbable polymers," *J. Neurosurg.* 86(6):1012-17 (1997).

Yiu, et al. "Glial inhibition of CNS axon regeneration," *Nat. Rev. Neurosci.* 7:617-627 (2006).

Zund, et al., "The in vitro construction of a tissue engineered bioprosthetic heart valve," *Eur. J. Cardiothorac. Surg.* 11(3):493-97 (1997).

\* cited by examiner

NON-CURLING POLYHYDROXYALKANOATE SUTURES

CROSS-REFERENCE TO RELATED APPLICATIONS

This application is a divisional of pending prior application U.S. Ser. No. 11/193,580, filed Jul. 29, 2005, entitled "Non-Curling Polyhydroxyalkanoate Sutures", by Said Rizk, which claims priority under 35 U.S.C. 119 to U.S. Ser. No. 60/598,296 entitled "Non-Curling Polyhydroxyalkanoate Sutures" by Said Rizk, filed on Aug. 3, 2004, all of which are herein incorporated in their entirety by reference.

STATEMENT REGARDING FEDERALLY SPONSORED RESEARCH OR DEVELOPMENT

This invention was made with U.S. government support under agreement 70NANB2H3053 awarded by the Department of Commerce, and agreements 1R43GM064863-01 and 2R44GM064863-02 awarded by the National Institutes of Health. The U.S. government has certain rights in the invention.

FIELD OF THE INVENTION

The present invention generally relates to fiber-based medical devices derived from poly-4-hydroxybutyrate and its copolymers.

BACKGROUND OF THE INVENTION

Poly-4-hydroxybutyrate (PHA4400) is a strong pliable thermoplastic that is produced by a fermentation process, as described in U.S. Pat. No. 6,548,569 to Williams et al. Despite its biosynthetic route, the structure of the polyester is relatively simple:

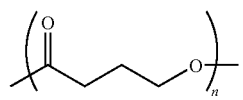

The polymer belongs to a larger class of materials called polyhydroxyalkanoates (PHAs) that are produced by numerous microorganisms. Steinbüchel, A., Polyhydroxyalkanoic acids, *Biomaterials,* 123-213 (1991); Steinbüchel A., et al., Diversity of Bacterial Polyhydroxyalkanoic Acids, *FEMS Microbial. Lett.* 128:219-228 (1995); and Doi, Y., *Microbial Polyesters* (1990). In nature these polyesters are produced as storage granules inside cells, and serve to regulate energy metabolism. They are also of commercial interest because of their thermoplastic properties, and relative ease of production. Several biosynthetic routes are currently known to produce PHA4400, as shown below:

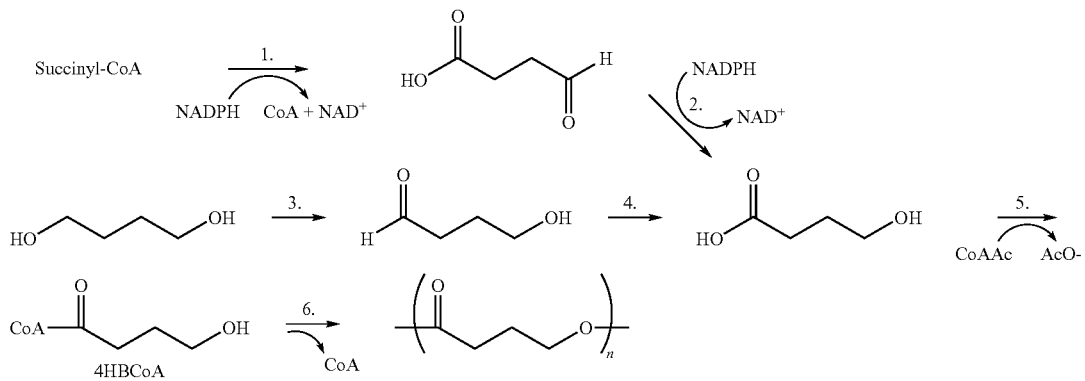

Chemical synthesis of PHA4400 has been attempted, but it has been impossible to produce the polymer with a sufficiently high molecular weight necessary for most applications (Hori, Y., et al., *Polymer* 36:4703-4705 (1995)).

Tepha, Inc. (Cambridge, Mass.) produces PHA4400 and related copolymers for medical use, and has filed a Device Master File with the United States Food and Drug Administration (FDA) for PHA4400. Related copolymers include 4-hydroxybutyrate copolymerized with 3-hydroxybutyrate or glycolic acid, as described in U.S. Pat. No. 6,316,262 to Huisman et al., and U.S. Pat. No. 6,323,010 to Skraly et al. Tepha, Inc. has also filed a Device Master File with the United States FDA for copolymers containing 3-hydroxybutyrate and 4-hydroxybutyrate. Methods to control the molecular weight of PHA polymers have been disclosed in U.S. Pat. No. 5,811,272 to Snell et al., and methods to purify PHA polymers for medical use have been disclosed in U.S. Pat. No. 6,245,537 to Williams et al. PHAs with degradation rates in vivo of less than one year have been disclosed in U.S. Pat. No. 6,548,569 to Williams et al. and WO 99/32536 by Martin et al. The use of PHAs as tissue engineering scaffolds has also been disclosed in U.S. Pat. No. 6,514,515 to Williams, and other applications of PHAs have been reviewed in Williams, S. F., et al., *Polyesters, III,* 4:91-127 (2002).

In the practice of surgery there currently exists a need for absorbable fibers and surgical meshes with improved performance. For example, an absorbable hernia mesh with prolonged strength retention could have many advantages over the non-absorbable synthetic meshes currently used in hernia operations (Klinge, U., et al., *Biomaterials* 22:1415-1424 (2001)). Long-term implantation of these non-absorbable meshes is not considered ideal because they can lead to complications such as adhesions (fistula formation), pain, and restriction of physical capabilities (Klinge et al., 2001). If implanted into surgical sites that are contaminated or have the potential to become contaminated, 50-90% of these non-absorbable implants will need to be removed (Dayton et al., Arch Surg. 121:954-960 (1986)). These implants are also not ideal for use in pediatric patients where they could hinder growth (Klinge et al., 2001). To date, the use of absorbable synthetic surgical meshes in hernia repair has been found to almost invariably result in large incisional hernias that require revision operations because of the relatively short-term strength retention of these materials (Klinge et al., 2001). However, an absorbable hernia mesh with prolonged strength retention could solve this problem by providing a mechanically stable closure, which can reduce the incidence of adhesions and the risks of infection, and is suitable for use in pediatric patients.

There are also needs for improved meshes and patches for other procedures. In pericardial repair there exists a need for a surgical material that will prevent adhesions between the sternum and heart following open-heart surgery. There are also similar needs to prevent adhesions in spinal and gynecology procedures that could be addressed with improved surgical meshes and patches.

Biomaterial patches derived from animal and human tissue are currently used in cosmetic surgery, cardiovascular surgery, general surgery (including hernia repair), and in urology and gynecology procedures for the treatment of conditions that include vaginal prolapse and urinary incontinence. There is a growing concern about the use of animal and human derived biomaterials because of the risks associated with disease transmission. However, the synthetic absorbable meshes and patches that are currently available are limited, can be inflammatory, and do not provide prolonged strength retention. Thus there exists a need to provide new absorbable meshes for these procedures as well. Ideally, these products should have prolonged strength retention, induce minimal inflammatory responses that resolve, have good handling properties, provide mechanically stable reinforcement or closure, offer anti-adhesion properties (where necessary), minimize the risks of disease transmission, and after absorption leave a healthy natural tissue structure.

Thus, there is a need to develop absorbable fibers with prolonged strength retention that could be used as suturing materials or as surgical meshes.

In 1984, a division of Johnson and Johnson (Ethicon) first introduced a monofilament synthetic absorbable suture made from polydioxanone (sold as PDS™). This suture retains about 50% of its strength up to six weeks after implantation, and is completely absorbed in the body within six months. Davis and Geck subsequently introduced a monofilament suture based on a copolymer of glycolide and trimethylene carbonate (sold as Maxon™). This suture has similar strength retention to PDS™. Two other monofilament sutures were introduced more recently: one based on segmented copolymers of glycolide and caprolactone (sold as Monocryl™), and the other based on a terpolymer of glycolide, p-dioxanone, and trimethylene carbonate (sold as Biosyn™). Monocryl™ is reported to have a 20-30% breaking strength after 2-3 weeks, and is completely absorbed after 3-4 months. Biosyn™ has an absorption profile similar to Monocryl™. Despite continued innovation in the development of absorbable synthetic monofilament sutures there is still a need for a synthetic absorbable suture with extended strength retention for patients requiring long-term wound support. For example, a monofilament suture with 50% strength retention at 3-6 months (after implantation). There are also limited options for synthetic absorbable meshes with prolonged strength retention.

U.S. Pat. No. 6,548,569 to Williams et al. discloses that PHA4400 has a slower absorption rate in vivo than many materials used as absorbable sutures, and provides absorption data for unoriented PHA4400 films and porous samples. Methods to produce medical fibers and textiles from PHA4400 have previously been described by Martin et al. in WO 2004/101002. These methods were successful in producing fibers with prolonged strength retention. WO 2004/101002 discloses poly-4-hydroxybutyrate polymer that can be converted into fibers and devices with tensile strengths comparable to existing absorbable synthetic fibers such as PDS but with prolonged in vivo strength retention. It does not, however, disclose pliable, curl free fibers with increased tensile and knot tying properties as compared to currently available absorbable fibers such as PDS nor methods to produce these important properties.

It is therefore an object of this invention to provide new fibers, surgical meshes, and medical devices with improved handling properties and improved knot tying properties.

It is another object of this invention to provide methods for fabricating the articles and devices.

SUMMARY OF THE INVENTION

Absorbable devices such as suture fibers, braids, and surgical meshes with improved handling and methods for making these materials have been developed. These devices are preferably derived from biocompatible copolymers or homopolymers of 4-hydroxybutyrate. The devices provide a wider range of in vivo strength retention properties than are currently available, and improved handling properties. The devices are processed using a method that produces a non-curling fiber useful as a suture. Properties are enhanced by the addition of a relaxation step following orientation and an annealing step. The relaxation and annealing steps are carried out at a temperature from about 30 to about 150° C. and from about 35 to about 150° C., respectively. Introduction of an annealing process and relaxation step for the fiber further enhances the handling properties of the resulting fibers. The relaxation step allows the fiber to shrink and elongation is allowed to increase by as much as 25% followed by an annealing step either on or offline to further control and fine tune elongation, modulus and strength. The poly-4-hydroxybutyrate may additionally be combined with absorbable additives then processed through relaxation and/or annealing to further enhance fiber handling.

In a preferred method, polymer fibers with improved handling and less tendency to curl are prepared by extruding the fiber, as described above, and then using an aging step whereby partially drawn polymer filament is stored from 2 to 72 hours at temperatures between 0 and −80° C. before processing with hot stretching and annealing, as described above.

In yet another preferred method, polymer fibers with improved handling may be prepared by blending up to 15% by weight calcium stearate, calcium phosphate or similar materials into the polymer and then melt extruding the polymer into the desired filaments. The filaments may be further processed by hot stretching and annealing, as described above.

DETAILED DESCRIPTION OF THE INVENTION

I. Definitions

"Strength retention" as generally used herein means the amount of time that a material maintains a particular mechanical property following implantation into a human or animal. For example, if the tensile strength of an absorbable fiber decreased by half over three months when implanted into an animal, the fiber's strength retention at three months would be 50%.

"Biocompatible" as generally used herein means the biological response to the material or device being appropriate for the device's intended application in vivo. Any metabolites of these materials should also be biocompatible.

"Handling" as generally used herein means the ease with which a material or device can be manipulated, particularly by a medical practitioner.

"Curling" as generally used herein means the tendency of a fiber to curve or form coils during handling.

"Non-curling" as generally used herein means has a reduced tendency to curve or form coils during handling.

"Pliable fiber" as generally used herein refers to a fiber with reduced stiffness.

"Knot Conversion" as generally used herein refers to the ratio of knot strength to the tensile strength.

"Knot Security" as generally used herein refers to the knot resistance to become undone.

"Poly-4-hydroxybutyrate" as generally used herein means a homopolymer comprising 4-hydroxybutyrate units. It may be referred to herein as P4HB, PHA4400 or TephaFLEX™ biomaterial (manufactured by Tepha Inc., Cambridge, Mass.).

"Copolymers of poly-4-hydroxybutyrate" as generally used herein means any polymer comprising 4-hydroxybutyrate with one or more different hydroxy acid units.

II. Fibers

A. Polymers

The filament may be formed from biodegradable polymers, such as poly-4-hydroxybutyrate (P4HB), and copolymers thereof, such as poly-4-hydroxybutyrate-co-poly-3-hydroxybutyrate (P4HB-P3HB) and poly-4-hydroxybutyrate-co-poly (glycolic acid) (P4HB-PGA). Tepha, Inc. of Cambridge, Mass. produces poly-4-hydroxybutyrate and copolymers thereof using transgenic fermentation methods.

B. Methods of Making Non-Curling Fibers

Methods of producing non-curling fibers with knot strength as high as 10 kg and improved straight to knot conversions (ratio of knot strength to tensile strength) have been developed. A polymer such as PHA4400 or copolymers thereof, is dried. Dried pellets of the polymer are melt extruded, then stretched in order to effect its orientation and thereby increase its tensile strength. The oriented fiber is then constrained between two godets and a heating media. The second godet rotates at a lower speed than the first, thereby allowing the fiber to shrink and relax. A third godet may be utilized before winding the fiber material. The relaxation step is carried out at a temperature from about 30 to about 150° C. In carrying out the annealing operation, the desired length of fiber may be wound around a creel, rack or skein and the wound material placed in a heating media maintained at the desired temperature to anneal the fiber. The annealing step is carried out at a temperature from about 35 to about 150° C. After a suitable period of residency in the heating media, the annealed fiber is then removed from the heating media and unwound. The resultant fiber is curl free, more pliable, has a higher knot strength and knot security.

In a preferred method, polymer fibers with improved handling and less tendency to curl are prepared by extruding the fiber, as described above, and then treated with an aging step whereby partially drawn polymer filament is stored from 2 to 72 hours at a temperature between 0 and −80° C. before processing with relaxation and annealing, as described above.

In yet another preferred method, polymer fibers with improved handling are prepared by blending up to 15% by weight calcium stearate, calcium phosphate or similar materials into the polymer and then melt extruding the polymer into the desired filaments. The filaments may be further processed through relaxation and annealing, as described above.

C. Filament Properties

Filaments prepared according to these methods are characterized by the following physical properties: (1) elongation to break from about 17% to about 85% (ii) Young's modulus of less than 350,000 psi, (iii) knot to straight ratio (knot strength/tensile strength) of 55-80%, or (iv) load to break from 1100 to 4200 g. These fibers exhibit a reduced tendency to curl and better knot and handling characteristics.

II. Applications for Non-Curling Filaments

The filaments can be used to form a wide range of medical products, including suture materials, stable surgical meshes, synthetic ligament and tendon devices or scaffolds. These fibers, both monofilament and multifilament, can be used to manufacture sutures with prolonged strength retention, as well as fiber-based medical devices such as surgical meshes and braids. Properties that can be improved through the use of these methods to decrease curling are lower Young's Modulus and an increase in straight to knot conversion. Modulus values are important to surgeons since soft, highly flexible sutures are easier to handle, use and tie. Flexible and slightly elastic sutures are also desirable since they conform to the wound and permit latitude in the tension applied to the suture by the surgeon.

The suture materials may be useful in the treatment of patients with diabetes, obesity, nutritional impairment, compromised immune systems, or other conditions such as malignancy or infection that compromise wound healing.

Stable surgical meshes can be used in procedures, such as pelvic floor reconstruction, urethral suspension (to prevent stress incontinence using the mesh as a sling), pericardial repair, cardiovascular patching, cardiac support (as a sock that fits over the heart to provide reinforcement), organ salvage, elevation of the small bowel during radiation of the colon in colorectal cancer patients, retentive devices for bone graft or cartilage, guided tissue regeneration, vascular grafting, dural substitution, nerve guide repair, as well as in procedures needing anti-adhesion membranes and tissue engineering scaffolds.

Further uses include combinations with other synthetic and natural fibers, meshes and patches. For example, the absorbable fibers and devices such as meshes and tubes derived from the fibers can be combined with autologous tissue, allogenic tissue, and/or xenogenic tissue to provide reinforcement, strengthening and/or stiffening of the tissue. Such combinations can facilitate implantation of the autologous, allogenic and/or xenogenic tissue, as well as provide improved mechanical and biological properties. Combination devices can be used, for example, in hernia repair, mastopexy/breast reconstruction, rotator cuff repair, vascular grafting/fistulae, tissue flaps, pericardial patching, tissue heart valve implants, bowel interposition, and dura patching.

The present invention will be further understood by reference to the following non-limiting examples.

Example 1

Melt Extrusion of PHA 4400

PHA4400 (Tepha, Inc., Cambridge, Mass.) (Mw 575K) was ground into small pieces using a Fritsch cutting mill (Pulversette 15, 10 mm bottom sieve) and dried under vacuum overnight to less than 0.01% (w/w) water. Dried pellets of the polymer were fed into an extruder barrel of an AJA (Alex James Associates, Greer, S.C.) ¾" single screw extruder (24:1 L:D, 3:1 compression) equipped with a Zenith type metering pump (0.16 cc/rev) and a die with a single hole spinnerette (0.026", 2:1 L:D) under a blanket of nitrogen. The 4 heating zones of the extruder were set at 140°, 190°, 200° and 205° C. The extruder was set up with a 15 ft drop zone, 48" air quench zone (10° C.), a guide roll, three winders and a pickup. The fiber was oriented in-line with extrusion by drawing it in a multi-stage process to provide fiber with high tensile strength and a reduced extension to break. The fiber was drawn in-line to stretch ratios of 6 to 11×. A spin finish (Coulston, Lurol PT-6A) was dissolved in isopropanol at 10% (v/v) and applied to the fiber before the first roll to act as a lubricant and protect the fiber during downstream processing. Molten polymer was then passed through a heated block to a metering pump and extruded from a die with a single hole spinneret. The block, metering pump and the die were maintained at a constant temperature, preferably 180-250° C. Pump discharge pressure was kept below 1500 psi by controlling the temperatures and the speed of the metering pump. The resulting spun extrudate filament was free from all melt irregularities. The extrudate was then drawn in a heated tube, which was maintained at a temperature above the melting temperature of the filament, quenched in a water bath, drawn through multistage orientation, and hot stretched, using a heated tube oven or hot liquid, preferably water, without the filament touching any surface until it is naturally cooled.

The highly oriented fiber passes through another heating unit maintained at a temperature from about 30° C. to about 150° C. The second heat treatment results in online relaxation, or shrinkage of the fiber. In order to accommodate this online shrinkage the exit fiber speed is allowed to be less than the feed speed by as much as 40%.

The relaxed fiber was wound on creels or racks and annealed for a preset time in an annealing media maintained at temperature from about 35° C. to about 150° C. After annealing, the fiber was allowed to reach room temperature and tested.

Example 2

Characteristics of Sutures Prepared in Example 1

Tensile mechanical properties of the melt extruded fibers were determined using a universal mechanical tester.

The mechanical properties of monofilament sutures prepared from non-curling fibers are shown in Table 1.

TABLE 1

Mechanical Properties of Monofilament Sutures Prepared from Non-Curling Fibers

| Size | Diameter mm | Load at Break g | Knot Tensile kg | Elongation % | Young's Modulus Psi |
|---|---|---|---|---|---|
| 3/0 | 0.278 | 4148 | 2.95 | 60 | 101,590 |
| 5/0 | 0.166 | 1800 | 1.31 | 64 | 123,600 |
| 6/0 | 0.105 | 1100 | — | 22 | 310,000 |

Surgical meshes were prepared with the sutures. Fabric construction was as follows: Mach #30 Raschel Knit 36 gauge fabric, 150 ends, 16 courses, 40 stitches per inch, using 18 needles per inch. Specifications for the finished fabric were: Weight: 58 g/m$^2$ (1.72 oz/sq. yard), Thickness: 0.29 mm.

The mechanical properties of surgical meshes knitted from non-curling fibers are shown in the Table 2.

TABLE 2

Mechanical Properties of Surgical Meshes Knitted from Non-Curling Fibers

| Samples Construction | Width (mm) | Thickness (mm) | Ball Burst (kg) | Extension at Peak (mm) | # Pores Per cm$^2$ | Density g/m$^2$ | Load per Density |
|---|---|---|---|---|---|---|---|
| No. 1 4 mil | 44.45 | 0.583 | 37.5 | 33.2 | 60 | 99 | 0.38 |
| No. 2 4 mil | 44.45 | 0.464 | 23.0 | 30.6 | 25 | 56 | 0.41 |
| No. 3 4 mil | 44.45 | 0.559 | 44.3 | 36.5 | 240 | 128 | 0.35 |
| No. 4 4 mil | 44.45 | 0.626 | 52.5 | 35.4 | 161 | 135 | 0.39 |
| No. 5 6 mil | 44.45 | 0.565 | 42.0 | 34.5 | 144 | 121 | 0.35 |

Those skilled in the art will recognize, or be able to ascertain using no more than routine experimentation, many equivalents to the specific embodiments of the invention described herein. Such equivalents are intended to be encompassed by the following claims.

I claim:

1. A polymeric filament comprising 4-hydroxybutyrate or copolymers thereof, wherein the filament has a knot strength to tensile strength ratio of 55-80%, an elongation to break from 17% to 85%, a Young's modulus of less than 350,000 psi, and a load at break between 1100 and 4200 g, and is produced by extrusion, orientation, relaxation, shrinking, and annealing of the extruded filament.

2. The filament of claim 1 wherein the filament has an elongation to break from 17% to 85%.

3. The filament of claim 1 wherein the filament has a Young's modulus of less than 350,000 psi.

4. The filament of claim 1 in the form of a suture.

5. The filament of claim 1 formed into a mesh.

6. The filament of claim 1 in the form of a medical device.

7. The filament of claim 1 in the form of a device for repair of tendons or ligaments.

* * * * *